(12) United States Patent
Krumdick et al.

(10) Patent No.: US 10,008,743 B2
(45) Date of Patent: Jun. 26, 2018

(54) HIGH VOLTAGE REDOX SHUTTLES, METHOD FOR MAKING HIGH VOLTAGE REDOX SHUTTLES

(71) Applicants: Gregory K. Krumdick, Homer Glen, IL (US); Trevor L. Dzwiniel, Carol Stream, IL (US); Krzysztof Pupek, Plainfield, IL (US)

(72) Inventors: Gregory K. Krumdick, Homer Glen, IL (US); Trevor L. Dzwiniel, Carol Stream, IL (US); Krzysztof Pupek, Plainfield, IL (US)

(73) Assignee: UCHICAGO ARGONNE, LLC, Chicago, IL (US)

(*) Notice: Subject to any disclaimer, the term of this patent is extended or adjusted under 35 U.S.C. 154(b) by 475 days.

(21) Appl. No.: 14/171,556

(22) Filed: Feb. 3, 2014

(65) Prior Publication Data

US 2015/0221982 A1    Aug. 6, 2015

(51) Int. Cl.
| | |
|---|---|
| H01M 10/0567 | (2010.01) |
| C07F 9/12 | (2006.01) |
| C07F 9/40 | (2006.01) |
| H01M 10/0525 | (2010.01) |
| C07F 9/42 | (2006.01) |
| H01M 10/42 | (2006.01) |

(52) U.S. Cl.
CPC ......... *H01M 10/0567* (2013.01); *C07F 9/12* (2013.01); *C07F 9/4021* (2013.01); *C07F 9/42* (2013.01); *H01M 10/0525* (2013.01); *H01M 10/4235* (2013.01); *H01M 2300/0025* (2013.01)

(58) Field of Classification Search
None
See application file for complete search history.

(56) References Cited

U.S. PATENT DOCUMENTS 4,065,504 A * 12/1977 Findlay ................. C07C 45/71
568/433
4,902,833 A * 2/1990 Moloy ................ C07F 9/5329
568/14
(Continued)

OTHER PUBLICATIONS

Abouzari-Lotf, Ebrahim, Ghassemi, Hossein, Shockravi, Abbas, Zawodzinski, Thomas, Schiraldi, David, "Phosphonated poly(arylene ether)s as Potential High Temperature Proton Conducting Materials", Polymer 52 (2011), pp. 4709-4717.*

*Primary Examiner* — Miriam Stagg
*Assistant Examiner* — Victoria H Lynch
(74) *Attorney, Agent, or Firm* — Cherskov Flaynik & Gurda, LLC

(57) ABSTRACT

The invention provides a method for producing a molecule capable of undergoing reduction-oxidation when subjected to a voltage potential, the method comprising phosphorylating hydroquinone to create a first intermediate; rearranging the first intermediate to an aryl-bis-(phosphonate) thereby creating a second intermediate comprising phosphorous alkoxy groups; alkylating (e.g., methylating) the second intermediate; converting the alkoxy groups to halides; and substituting the halides to alkyl or aryl groups. Also provided is a system for preventing overcharge in a Lithium-ion battery, the method comprising a mixture of a redox shuttle with electrolyte in the battery such that the shuttle comprises between about 10 and about 20 weight percent of the mixture.

12 Claims, 7 Drawing Sheets

Example 1: R = Et. RS51. MW = 346.34
Example 2: R = n-Pr. RS52. MW = 406.39
Example 3: R = Ph. RS53. MW = 538.51
Example 4: R = Me. RS54. MW = 290.23
Example 5: R = 4-F-Ph. RS55. MW = 610.47

(56) References Cited

U.S. PATENT DOCUMENTS

| | | |
|---|---|---|
| 5,858,324 A | 1/1999 | Dahn et al. |
| 5,900,385 A | 5/1999 | Dahn et al. |
| 6,143,268 A | 11/2000 | Dahn et al. |
| 6,680,145 B2 | 1/2004 | Obrovac et al. |
| 6,964,828 B2 | 11/2005 | Lu et al. |
| 7,078,128 B2 | 7/2006 | Lu et al. |
| 7,211,237 B2 | 5/2007 | Eberman et al. |
| 2003/0027048 A1 | 2/2003 | Lu et al. |
| 2004/0121234 A1 | 6/2004 | Le |
| 2004/0179993 A1 | 9/2004 | Dahn et al. |
| 2006/0045144 A1 | 3/2006 | Karlsen et al. |
| 2011/0294017 A1* | 12/2011 | Weng .................... H01G 9/038 429/338 |

* cited by examiner (Step I)

(Step II)

(Step III)

(Step IV)

HIGH VOLTAGE REDOX SHUTTLES, METHOD FOR MAKING HIGH VOLTAGE REDOX SHUTTLES

The U.S. Government has rights in this invention pursuant to Contract No. DE-AC02-06CH11357 between the U.S. Department of Energy and the University of Chicago representing Argonne National Laboratory.

BACKGROUND OF THE INVENTION

1. Field of the Invention

This invention relates to high voltage lithium ion battery components and more particularly this invention relates to high voltage reduction-oxidation shuttles and methods for their production.

2. Background of the Invention

Lithium ion batteries provide the best option to date for portable electric power. Their safety compared to early lithium batteries is multi-fold, and include the minimization of lithium metal within the battery. Whereas solid lithium comprised the anode (negative electrode) of the first lithium batteries, the anodes of lithium ion batteries comprise graphite or other intercalating media adapted to receive lithium cations.

Unlike lithium metal, which is still used in primary batteries, lithium ion ($Li^+$) is very stable and unreactive. When intercalated in the negative electrode, its potential is much lower than when in the positive electrode (this difference of potential is the source of energy in every battery) but explosive reactivity is eliminated. The battery works with lithium ions shuttling from one electrode to the other through an electrolyte solution. They move spontaneously from the negative to the positive electrode during discharge giving up the energy stored. During the recharge process energy is spent relocating those ions back in the negative electrode.

During discharge, lithium ions spontaneously shuttle from the negative insertion electrode into the electrolyte and from the electrolyte into the positive insertion electrode. The electrolyte allows the diffusion of ions but prevents electrons flow. At the same time electrons spontaneously flow from the negative to the positive electrode: through the load. As discharge proceeds the potential (E) of each electrode shifts resulting in a decreasing difference between them and thus to a decreasing voltage as charge (Q) exits the battery.

During charge, lithium ions are forced out of the positive into the electrolyte and into the negative electrode. Electrons are injected into the negative and taken from the positive electrode. In doing the negative potential becomes more negative and the positive more positive, thus increasing the difference of potential which can be equated to the voltage.

Invariably, more energy goes into charging than what is provided in discharge. A goal of the invention is minimizing that difference.

Lithium ion batteries provide superior reversibility during charge/discharge cycles; longer battery lives result. However, care must be taken to prevent overcharging, as battery components (e.g., the positive electrode or cathode), can be otherwise damaged. This is becoming more relevant as newer high voltage cathode materials start to emerge. For example, while voltage limits for initial Li-ion batteries rarely exceeded 3.6 V, it is not unusual to see voltages in the range of 4.2 V and 4.5 V now being required in the automotive and aviation industries. About 3.6 V is nominal for commercial Li-ion batteries, 4.2 V is the highest seen commercially, and 4.5 V is seen in experimental, not yet commercialized cathode materials.

Attempts to prevent overcharge include the use of Battery Management Systems (BMS) and similar electronic devices. BMS comprises a circuit board that protects a cell from cell overvoltage and under voltage as well as current discharge and charge. If a short occurs in the wiring between the cells and the BMS, a thermal runaway could result from overcharging or from external excessive loading, as has been postulated in recent airliner electrical system malfunctions.

In light of the foregoing, nonmechanical systems for preventing battery malfunctions have been investigated. For example, chemical additives known as reduction-oxidation (redox) shuttles are often mixed in with battery electrolyte to absorb excess charge and protect the electrodes during recharge. The intention is for these redox moieties to "shuttle" the current and prevent the voltage applied during recharge from increasing past the potential of the shuttle. To date, there are no viable high voltage shuttles.

However, state of the art processes for producing redox-shuttles for lithium ion batteries require expensive starting materials, which are in many cases hazardous. For example, a current shuttle production protocol utilizes chloro-diisopropyl phosphine and 1,4-dibromo-2,5-dimethoxybenzene. Also, cryogenic conditions (−78 C) are required to minimize side reactions, which would otherwise occur as the current production protocols are very exothermic. As a consequence of these drawbacks, the costs for producing more than small amounts of the shuttles is prohibitive. Therefore, industrial scale up has been hampered.

A need exists in the art for an economic method for producing redox shuttles that emphasizes scalability for use in lithium-ion batteries. The method should not require expensive or hazardous chemicals or generate extensive secondary waste streams. The method should produce redox shuttles with enhanced solubilities compared to state of the art shuttles, so as to confer greater overcharge protection at higher voltages and higher current rate.

SUMMARY OF INVENTION

An object of the invention is to provide a method for producing electrolyte redox shuttles that overcomes many of the disadvantages of the prior art.

Another object of the invention is to provide a method for producing redox shuttles for lithium ion batteries. A feature of the invention is that the method manipulates nonhazardous materials at temperatures no lower than −15° C. to produce the shuttles. An advantage of the method is that the redox shuttles are produced economically in industrial quantities.

Still another object of the present invention is to provide a method to produce industrial quantities of redox shuttles. A feature of the present method is that it replaces the oxidation step, the halogenated solvents and cryogenic requirements of previous protocols. An advantage of the invented method is that it ultimately produces shuttles having more than 99 percent purity after a single recrystallization step.

Yet another object of the present invention is to provide a redox shuttle for lithium batteries. A feature of the invention is that the redox shuttle produced has about a 15 weight percent solubility in electrolyte. An advantage of the invention is that the increased solubility increases the electrolyte's capacity to move excess charge between electrodes without damage to the electrodes or electrolyte. Another advantage is that the shuttles can be used in conjunction with mechanical BMS or without BMS or any other means for shuttling charge.

Briefly, the invention provides a method for producing a molecule capable of undergoing reduction-oxidation when subjected to a voltage potential, the method comprising phosphorylating hydroquinone to create a first intermediate; rearranging the first intermediate to an aryl-bis-(phosphonate) thereby creating a second intermediate comprising phosphorous alkoxy groups; methylating the second intermediate; converting the alkoxy groups to halides; and substituting the halides to alkyl or aryl groups.

Also provided is a system for preventing overcharge in a Lithium-ion battery, the method comprising a mixture of a redox shuttle with electrolyte in the battery such that the shuttle comprises between about 1 and about 30 weight percent of the mixture, preferably between about 5 and about 25 percent, and most preferably between about 10 and about 20 percent. An embodiment of the invention displayed a 15 weight percent solubility in an electrolyte comprising 1.2 M $LiPF_6$ in ethylene carbonate/diethyl carbonate (3:7 by weight).

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invented method confers several benefits viz the prior art. Unlike previous shuttle synthesis protocols, all of the reagents used in the instant method are commercial commodity chemicals. Also, no cryogenic reactions are required. In an embodiment of the invention, only one relatively low temperature process (−25 C) is envisioned. The processes are more selective and less energetic than the previous art, allowing the invention to run at milder temperatures.

A salient feature of the invention is that the method requires no oxidations. As such, no peroxides are required in the synthesis. Rather, the final oxidation state of the product is set from the onset of the process. Oxidation reactions often create high exotherms, i.e, cause increases in reaction temperatures which must be controlled to prevent product degradation and to facilitate scalability to industrial scale production.

Figure 1:
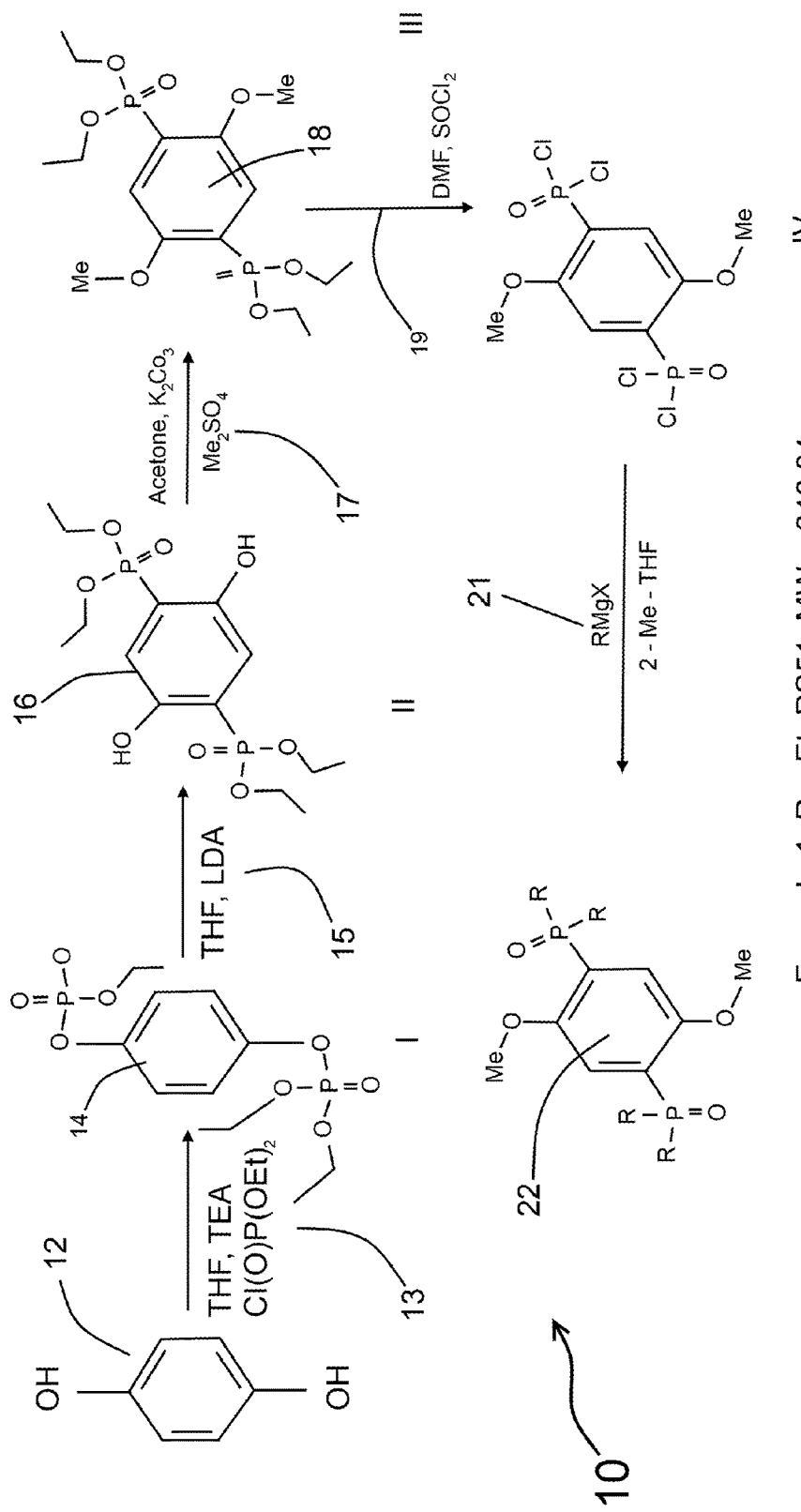
FIG. 1 is a schematic of the synthesis of redox shuttle, in accordance with features of the present invention.
Figure 3:
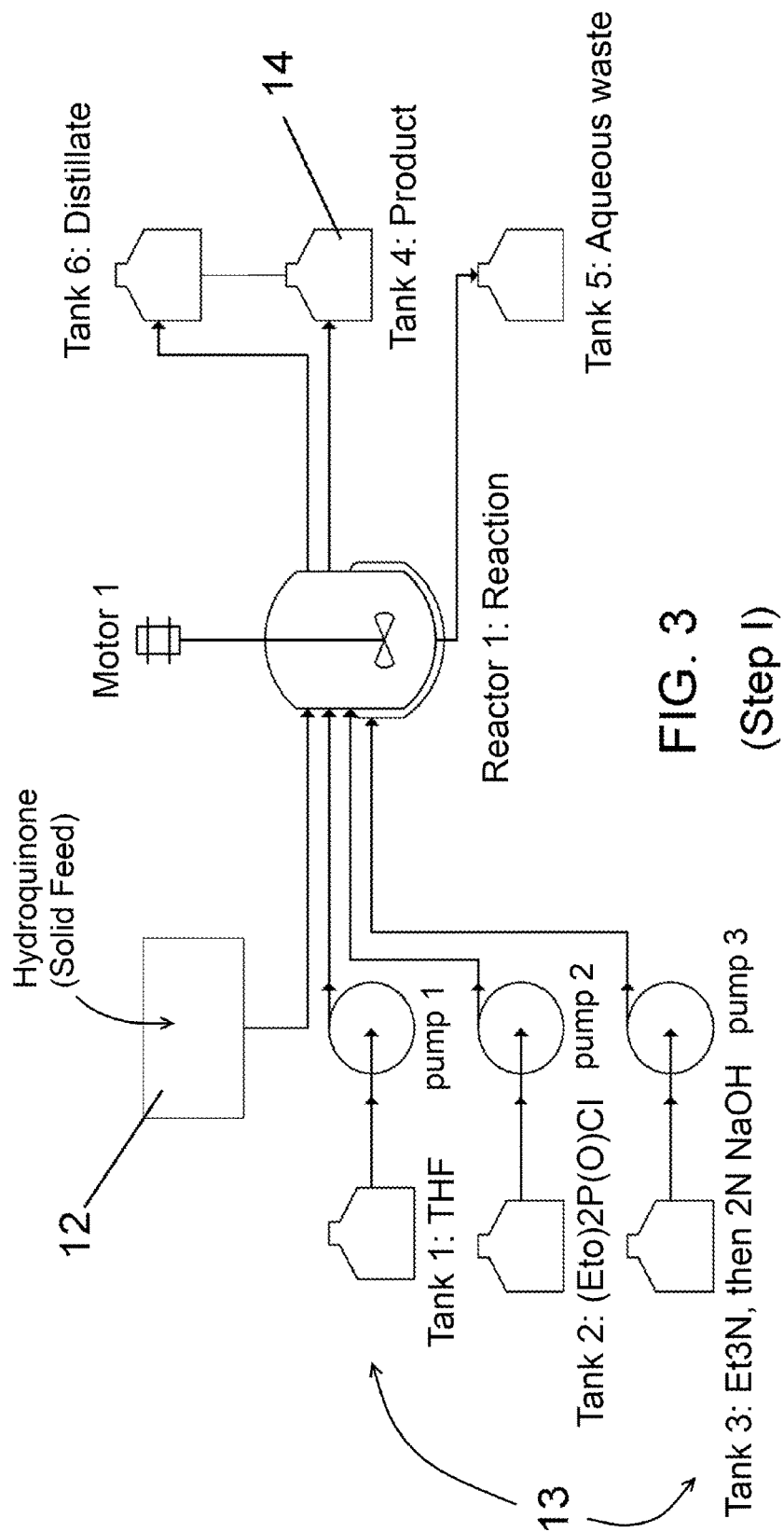
FIG. 3 is a schematic diagram of first intermediate of synthesis (Step I) toward production of a redox shuttle, in accordance with features of the present invention.

FIG. 1 depicts an embodiment of the method, the method designated as numeral 10. Hydroquinone 12 is first phosphorylated to form a first intermediate. This first intermediate synthesis is further elaborated in FIG. 3, wherein relatively economical reactants 13 (tetrahydrofuran, dialkyl halide-phosphates, and trialkylamines) are utilized.

Figure 4:
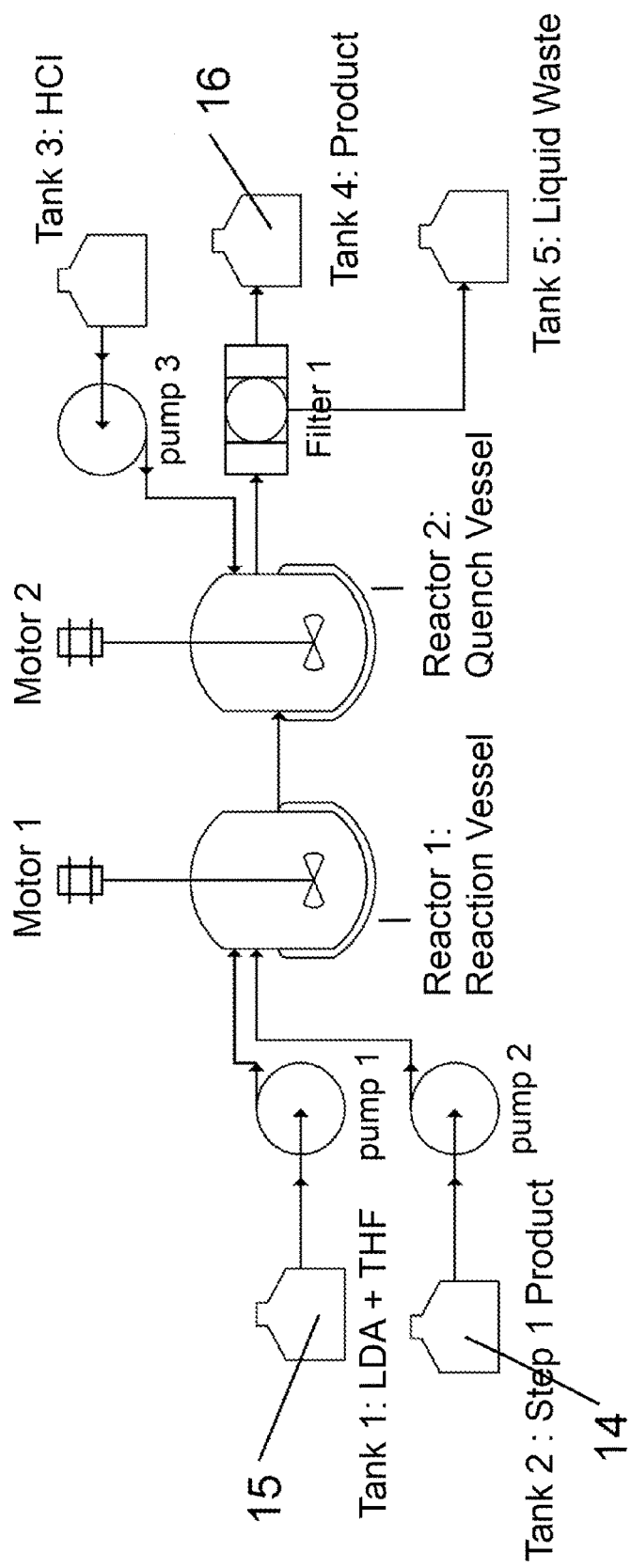
FIG. 4 is a schematic diagram of second intermediate synthesis (Step II) toward production of a redox shuttle, in accordance with features of the present invention.

The resulting phosphorylated compound 14 is rearranged to an aryl-bis-(phosphonate), thereby forming a second intermediate 16 in Step II. Generally, this is accomplished by using strong base capable of deprotonating the intermediate 14 at the ortho positions relative to the phosphoryl groups. In one embodiment, the intermediate 14 is mixed with reactants 15 (lithium amides and additional THF). FIG. 4 is a schematic of the Step II process.

Figure 5:
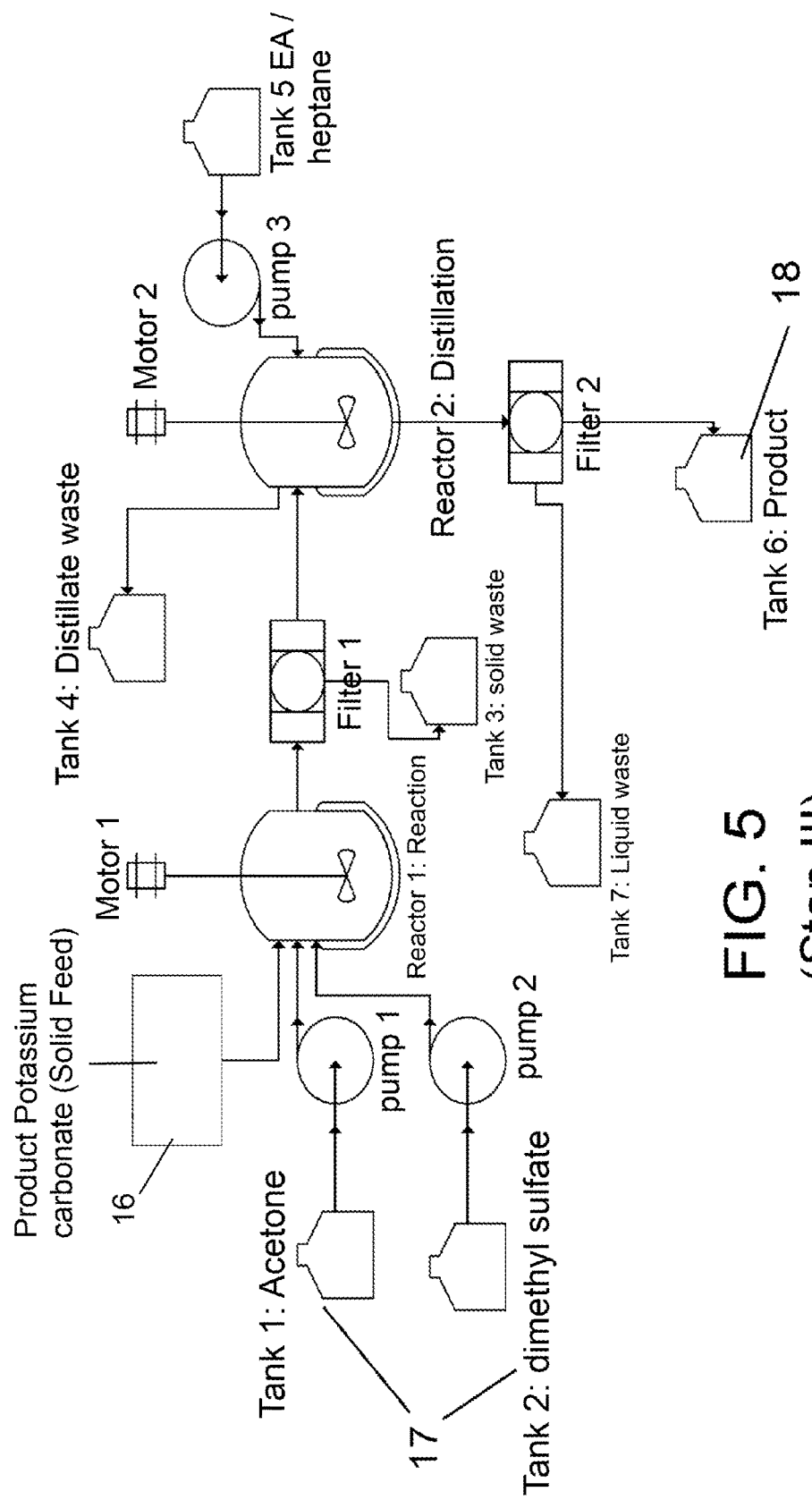
FIG. 5 is a schematic diagram of synthesis of alkylated (e.g., methylated) moiety in a synthesis of a redox shuttle (Step III), in accordance with features of the present invention.

Hydroxyl groups of this phosphate are then alkylated (e.g. methylated (Me)), 18 in Step III. Otherwise, the original hydroxyl groups would interfere with both the subsequent chemistry as well as the battery. Converting to methoxy groups removes the acidic H atom that causes these problems. Aside from methyl moieties, other alkyl groups are suitable, including but not limited to ethyl-, propyl- and butyl-moieties. Reactants 17 used in this Step III (depicted as FIG. 5) include, but are not limited to, ketones, d-alkylated sulfates and carbonates. The reactants can be any alkylation reagent (alkyl halides, alkyl sulfonates, alkyl carbonates, and combinations thereof.

Figure 6:
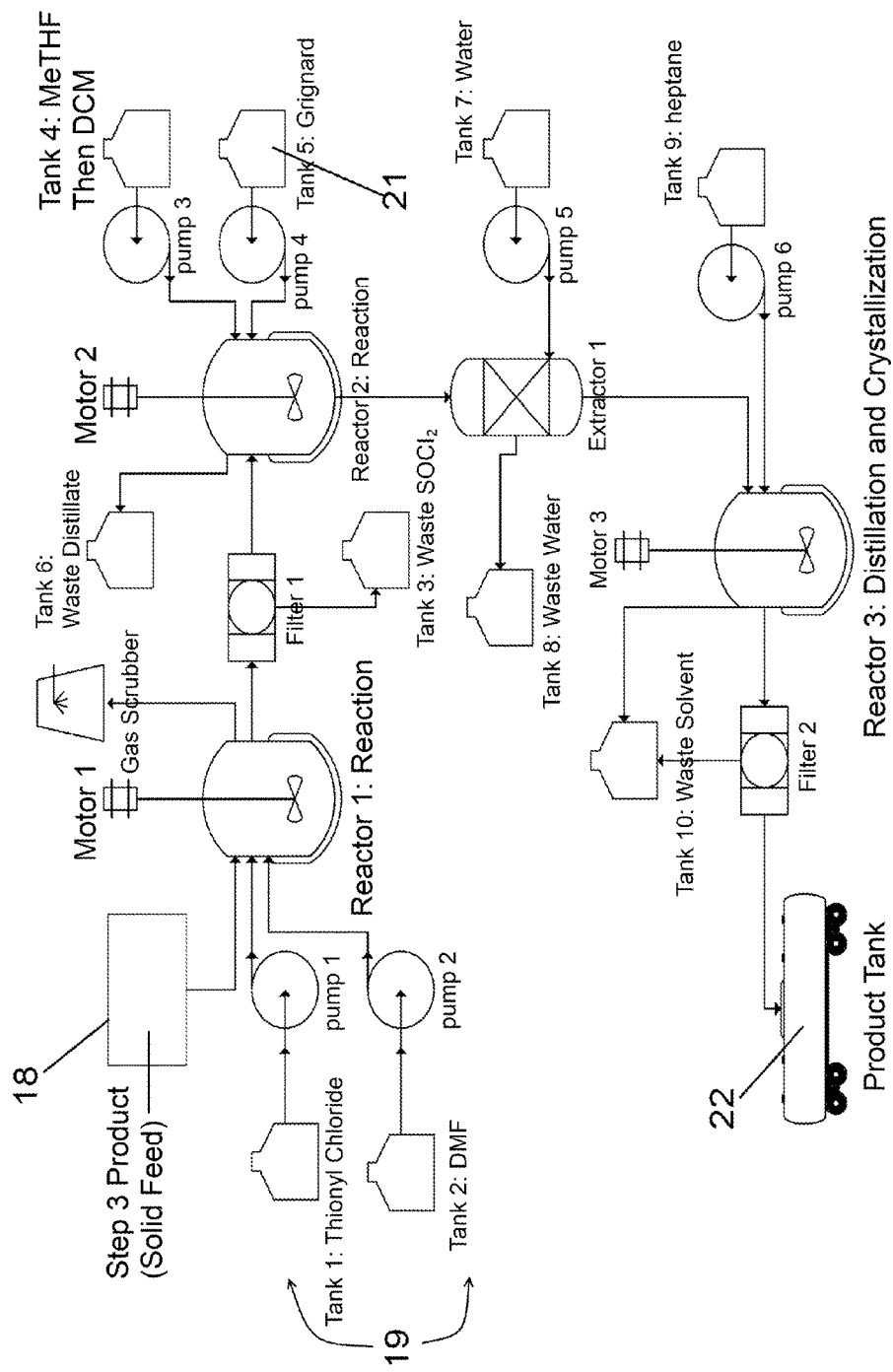
FIG. 6 is a schematic diagram of fabrication of halogenated intermediate and then toward synthesis of a redox shuttle in accordance with features of the present invention.

The resulting phosphorous alkoxy groups are then halogenated 20 (e.g., chlorinated) in Step IV, with those halogen groups leaving via a Grignard reagent to yield phosphorylated compounds substituted with alkyl or aryl groups 22. This penultimate and final step of the invented method is depicted in the schematic diagram designated as FIG. 6. Suitable final substitution alkyl or aryl groups are designated on FIG. 1 below the final product 22 generated and include, but are not limited to, methyl-, ethyl-, propyl-, phenyl-, and 4-fluorophenyl.

Halogenation of two phosphorous groups on the same molecule was unexpected, particularly given the starting compound 18 depicted in FIG. 1.

In operation, the invented redox shuttle is a charge transfer mechanism for Li-ion battery overcharge protection. When the battery is overcharged, the redox shuttle is oxidized by losing an electron to the positive electrode (i.e. cathode). The radical cation formed is then diffused back to the negative electrode (i.e. anode) causing the cation to obtain an electron and be reduced. The net reaction shuttles electrons from the positive electrode to the negative electrode without causing chemical damage to the battery. These results were repeated over several cycles.

The invented shuttle can be used with a myriad of cathode materials, including spinel, olivine, carbon-coated olivine, $LiMnPO_4$, $LiMn_2O_4$, $LiCoPO_4$, $LiCoO_2$, $LiFePO_4$, $LiCoO_2$, $LiNiO_2$, $LiNi_{i-x}Co_yMet_zO_2$, $LiMn_{0.5}Ni_{0.5}O_2$, $LiMn_{<)_{-.3}}Co_{0.3}Ni_{0.3}O_2$, $LiMn_2O_4$, $LiFeO_2$, $LiMet_{0.5}Mni_{.5}O_4$, $Li_{1+x'}Ni_aMnpCo_yMet'_5O_{2-z}F_z$, $A_n B_2(XO_4)_3$ (Nasicon), vanadium oxide, or mixtures of any two or more thereof, wherein Met is Al, Mg, Ti, B, Ga, Si, Mn, or Co; Met' is Mg, Zn, Al, Ga, B, Zr, or Ti; A is Li, Ag, Cu, Na, Mn, Fe, Co, Ni, Cu, or Zn; B is Ti, V, Cr, Fe, or Zr; X is P, S, Si, W, or Mo; and $0<x<0.3$, $0<y<0.5$, $0<z<0.5$, $0<x'<0.4$, $0<\alpha<1$, $0<\beta<1$, $0<\gamma<1$, $0<\delta<0.4$, $0<z'<0.4$, and $0<n'<3$. Other cathode materials include lithium transition metal oxides such as those disclosed in U.S. Pat. Nos. 5,858,324; 5,900,385; 6,143,268; 6,964,828; 7,078,128; 7,211,237; and 6,680,145, and U.S. Pat. Application Nos. 2003/0027048; 2004/0121234; 2004/0179993; and 2006/045144; and combinations of any two or more such materials.

The invented shuttle exhibits approximately up to 15 percent solubility in electrolyte such that 15 weight percent of the electrolyte shuttle mixture comprises the shuttle. Suitable electrolyte solutions include any suitable electrolyte solvent/mixture of solvents including but not limited to carbonate compounds selected from the group consisting of dimethyl carbonate, diethyl carbonate, ethyl methyl carbonate, ethylene carbonate, propylene carbonate, divinylcarbonate, and combinations thereof.

Figure 2A:
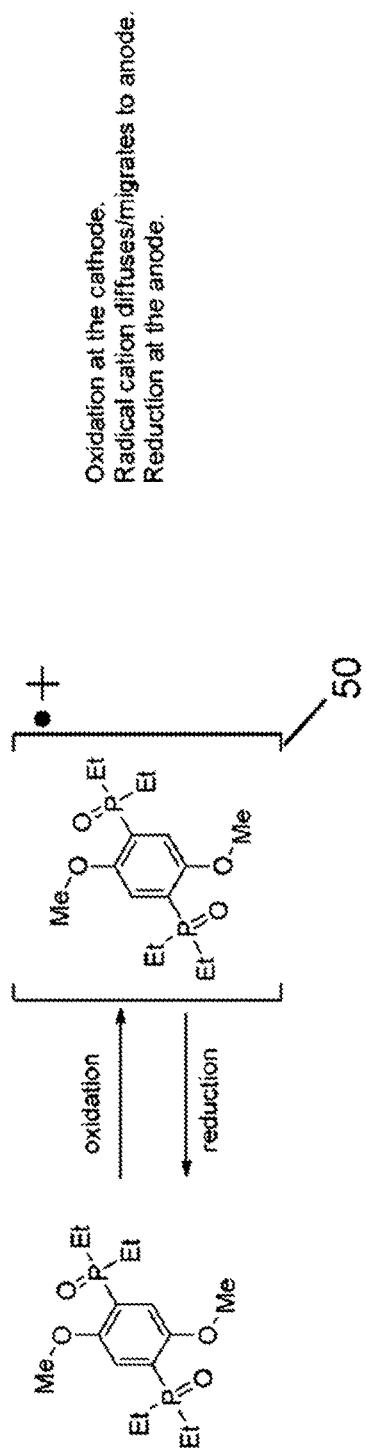
FIG. 2A is a depiction of the radicals formed by the shuttle during charge and discharge, in accordance with features of the present invention.
Figure 2B:
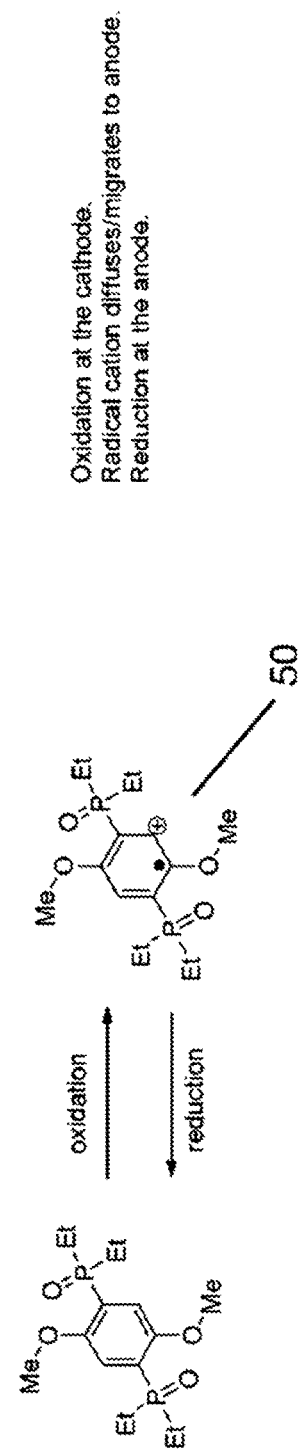
FIG. 2B is a specific description of the radicals formed by the shuttle during charge and discharge, in accordance with features of the present invention.

FIG. 2A is a schematic generalized depiction of the redox reaction experienced by the invented shuttle in situ, designated therein as numeral 50. A possible resonance scenario, shown in FIG. 2B, has the aromatic ring of the alkyl or aryl substituted phosphorylated compound participating in the charge separation. This scenario has the positive charge center located at the third position on the ring while the negative charge center or hole is located at the fourth position on the ring. It is this cation that migrates back toward the anode.

Without the benefit of the redox solute, the cation of the salt comprising the cathode (e.g., the cobalt in the $Li_{1.2}Ni_{0.15}Co_{0.1}Mn_{0.55}O_2$ or the manganese in the $LiMn_2O_4$) decomposes, thereby resulting in irreversible damage and/or thermal runaway of the battery.

The invented method is a preferred alternative to the hazardous protocols currently relied on to produce redox shuttles. For example, the lowest temperatures of the entire protocol range from between approximately –10 C and approximately –20 C and typically about –15 C, compared to the –78 C required in state of the art processes.

Solvents utilized in the instant protocol are relatively "green" (such as acetone and 2-methyltetrahydrofuran, compared to the halogenated diethyl ethers, and dichloromethanes heretofore required.

Chemical hazards associated with the instant method are relatively minor (air sensitive only) compared to the relatively intense hazards presented by the peroxides and pyrophorics required in the prior art. As such, raw material costs of the invented method are less than one tenth those of the prior art (e.g. $15/gram versus more than $200/gram.). The high costs and relatively limited supply of the previous shuttle raw materials presents a sourcing concern when scaling up is required. For example there are a very limited number of dialkylchlorophosphine starting materials that are commercially available. In contrast, there is a wide range of commercial alkyl or arylmagnesium halides (element 21, FIG. 1) that can be used in the invented method to develop the shuttle and related compounds.

Purification of the resulting redox shuttle is effected via recrystallization, compared to the equipment and solvent intensive chromatography methods required heretofore. Specifically, the invented protocol generates shuttle without the need to remove excess by-products, such that no silica gel or other adsorbents are required. Rather, a single crystallization step yields product having purity in access of 99 percent.

Surprisingly and unexpectedly, the resulting redox shuttle exhibits greater solubility compared to a previously produced shuttle which features isopropyl groups flanking the phosphonate moiety. The instant shuttle features smaller alkyl groups (methyl and ethyl groups as designated in the rectangles in the compound 22 of FIG. 1) flanking the same moiety. Inasmuch as smaller alkyl groups usually connote less solubility, the increased solubility of the smaller alkyl version of the shuttle is counter intuitive viz the chemical arts.

FIGS. 3-6 are schematic diagrams of phases I-IV of the shuttle method depicted in FIG. 1.

Example 1

The following example is an exemplary embodiment of the invented method and resulting product.

Step I
Synthesis Detail

A glass reactor (20 L, jacketed, e.g., Chemglass) equipped with drain valve, internal temperature probe, reflux condenser, gas inlet/outlet adapters and powder port was flushed with argon. The jacket of the reactor was connected to a Huber heating/chilling circulator. An argon flow was continued to inert the reactor. The reactor was charged with hydroquinone (265 g), THF (4 L) and diethyl chlorophosphate (995 g). The process temperature was set to 18° C. Triethylamine (1 L) was added via peristaltic pump at 10 mL/min. A light blue suspension formed within 20 minutes. The reaction was stirred overnight and cooled to about –2° C. MTBE (2 L) was added. The reaction was quenched by the addition of 2 L of 2M NaOH. The layers were separated and the organic layer washed with additional 2M NaOH (2×2 L). The organic layer was then rotovaped to a purple oil. The oil was cooled to room temperature (RT) and filtered through a sintered glass frit to remove final amounts of solids. A nearly odorless purplish oil was obtained at 100 percent yield of the reaction.

Step II
Synthesis Detail

A 2 L three neck flask was purged with nitrogen. Commercial lithium diisopropylamide (1 bottle, 800 mL, 2M in THF/heptane/ethyl benzene) was charged to the flask. The solution was cooled to –25° C. A solution of 1,4-phenylene tetraethyl bis(phosphate) (250 g) in THF (250 mL) was added (for example via peristaltic pump) over 90 minutes. The suspension was allowed to warm to room temperature. The solution was then quenched by slow addition into cold 25 percent aqueous HCl. The white precipitate was filtered and washed with water (400 mL) and MTBE:heptane (1:1, 500 mL). The solids were dried in an open tray to provide better than 75 percent yield, and specifically 76 percent.

Two more reactions were run according to the above procedure to yield 60 percent yield and 72 percent yield. Then, the combined materials from the three reactions were slurried in hot methanol (1.2 L) for 1 hour. The mixture was cooled to 12° C. and filtered. After washing with methanol (200 mL) and drying, about 50 percent overall yield) remained.

There are several methods and conditions for converting hydroquinone to intermediate. For example, the synthesis detail of the first two intermediates are minor modifications of procedures found in Ortho-Hydroxyaryl Diphosphonic Acids Dhawan, B. and Redmore, D. *J. Org. Chem.* 1984, 49, 4018-4021, the entirety of which is incorporated by reference herein.

Step III
Synthesis Detail

Phenol methylation occurred as follows: A 2 L four necked flask with reflux condenser, thermocouple, mechanical stirrer and addition funnel was charged with tetraethyl (2,5-dihydroxy-1,4-phenylene)bis(phosphonate) (150 g, lot TD5-125) and acetone (1.2 L). The mixture was stirred and heated to 55° C. to give a distinct yellow suspension. Dimethyl sulfate (63 mL) was added. The mixture was heated overnight and then dimethyl sulfate were added piecemeal (e.g. 11 ml in 3 portions) until the HPLC showed a complete reaction and the suspension was no longer yellow. The mixture was cooled and filtered. The filtrate was rotovaped to an oil. The oil was redissolved in ethyl acetate (150 mL) and heptane (150 mL) was added. The solution was rotovaped dry to give an off-white solid (163 g, 102%).

The suitable temperature of this process was below the boiling point of the solvent, generally with about 20 to about 60° C. and more specifically about 55° C. Equivalents dimethyl sulfate: 1.7, range of 1.5 to 3.0.

Shuttle Synthesis
Detail

A 2 L 3 neck flask was charged with tetraethyl (2,5-dimethoxy-1,4-phenylene)bis(phosphonate). A mechanical stirrer, thermocouple, and reflux condenser were used. The flask was purged with nitrogen and the outlet gasses send to a $NaOH_{(aq)}$ trap. The solids were dissolved in thionyl chloride and the solution was heated to 65° C. with stirring at 220 rpm. N,N-Dimethylformamide (4 equiv) was added via peristaltic pump at a rate of 25 mL/hour. The solution was kept at temperature for about 14 hours. The mixture was then cooled to room temperature.

The solids that precipitated from the reaction mixture were filtered under inert atmosphere (e.g. nitrogen), washed with toluene and dried under a nitrogen stream to give an off-white powder. Reaction Concentration: 2.5 mL/g, range of 1.0 to 10.0. Temperature: 65° C., range of 50-80° C. (boiling point is 75° C.). The time for converting to the P-halide intermediate ranged from 6-48 hours, with conversion normally occurring in about 12 to 16 hours.

The crude intermediate was slurried in 2-methyltetrahydrofuran, then cooled to between about 0 and about −10° C. Ethylmagnesium bromide (3M, ether at about 4.6 equiv) was added to keep the temperature between about 0 and about −10° C. The reaction was then allowed to warm to room temperature and stirred overnight, after which the mixture was quenched with methanol. The solvents were removed via negative pressure (e.g., using a rotovap). The residue was then re-slurried in dichloromethane and extracted with 10 percent aqueous HCl. Additional water was then added to thin out the thick creamy slurry. Dichloromethane was then used to extract the water-soluble product. The combined extracts were dried on the rotovap to give a total of about 94 percent of solid. Reaction Concentration: 6 ml/g, range 3-15. Temperature was maintained at from about 0° C. to about −10° C., with a suitable temperature range of between about −30 to 30° C. Reaction time was about 12 hours, with a suitable reaction time of between about 2 and 24 hours.

Recrystallization
Detail

The crude reaction products were slurried in acetone. The slurry was then filtered and washed with acetone to yield a white powder.

The material was then dissolved in dichloromethane and filtered to remove some fines. Hexane was added over time (for example, over 30 minutes using a peristaltic pump). The precipitates were stirred and filtered to give the first crop. A second crop was obtained by cooling and re-filtering to give another yield. The two crops were analyzed and combined to give the final material. The mother liquor was separately rotovaped dry to yield 94 percent pure material.

The process yielded a final step crude yield of about 85 percent. A final step pure yield was approximately 53 percent. Overall yield from hydroquinone feedstock was 27 percent. Purity of the final product was between 99 and 99.5 percent, and more typically about 99.2 percent. An embodiment of the invention yielded 99.16 percent (average HPLC peak area integration). GC/MS>99.9% peak area, m/z 346. Melting point was about 238-241° C. $^1H$, $^{13}C$, $^{31}P$ NMR agree with the structure 22 depicted in FIG. 1.

The shuttle formed in this Example 1 was (2,5-dimethoxy-1,4-phenylene)bis (diethylphosphine oxide).

Example 2

A 250 mL 3 neck flask was charged with tetraethyl (2,5-dimethoxy-1,4-phenylene)bis(phosphonate) (25.46 g, lot TD50129). A thermocouple and reflux condenser were attached. The flask was purged with inert gase (e.g., nitrogen) and the outlet gasses send to a $NaOH_{(aq)}$ trap. The solids were dissolved in thionyl chloride (75 mL) and the solution was heated to 65° C. with stirring. N,N-Dimethylformamide (19 mL, 4 equiv) was added via syringe pump over 1 hour. The solution was kept at temperature for 14 hours. The mixture was then cooled to room temperature.

The solids that precipitated from the reaction mixture were filtered under nitrogen and washed with toluene (2×20 mL) and MTBE (20 mL) and dried under a nitrogen stream for a time sufficient to yield substantially moisture free precipitate. (e.g., a drying protocol involves drying for about one hour to give an off-white powder. This material was split into two reactions.

The crude intermediate was slurried in 2-methyltetrahydrofuran (95 mL). The mixture was cooled to between about 0 and about −10° C. n-Propylmagnesium bromide (2M, ether, 6 equiv) was added at a rate to keep the temperature between about 0 and about −10° C. The reaction was then allowed to warm to room temperature and stirred overnight. The mixture was then quenched with methanol. The solvents were removed on the rotovap. The residue was then re-slurried in 100 mL dichloromethane and extracted with 100 mL 10 percent aqueous HCl. Additional water was then added to thin out the thick creamy slurry. Dichloromethane was then used to extract the water-soluble product. The combined extracts were dried on the rotovap. The solids were slurried in acetone (20 mL) and filtered to give an off-white solid (about 49 percent yield). The crude solid was recrystallized from ethyl acetate to yield more than 98 percent (e.g. 98.2%) HPLC purity. This was recrystallized again from DCM/heptane. A final total of 31 percent yield was obtained. With a purity again better than 98 percent (e.g., 98.53 percent, given an average HPLC peak area integration). GC/MS>99.9% peak area, m/z 402. Melting point 250-252° C. $^1$H, $^{13}$C, $^{31}$P NMR agree with the proposed structure.

The shuttle formed in this Example 2 was (2,5-dimethoxy-1,4-phenylene) bis(dipropylphosphine oxide).

Example 3

A 250 mL 3 neck flask was charged with tetraethyl (2,5-dimethoxy-1,4-phenylene)bis(phosphonate) (10.0030 g, lot TD50127). A thermocouple and reflux condenser were attached. The flask was purged with an inert gas and the outlet gasses send to a NaOH$_{(aq)}$ trap. The solids were dissolved in thionyl chloride (25 mL) and the solution was heated to 65° C. with stirring. N,N-Dimethylformamide (7.5 mL, 4 equiv) was added via syringe pump over 1 hour. The solution was kept at temperature for 14 hours. HPLC showed some starting material. Additional DMF and SOCl$_2$ were added. The mixture was then cooled to room temperature.

The solids that precipitated from the reaction mixture were filtered under nitrogen and washed with MTBE (2×20 mL) and dried under a nitrogen stream for 1 hour to give an off-white powder (10.3 g, theoretical 9.1 g).

The crude intermediate was slurried in 2-methyltetrahydrofuran (50 mL). The mixture was cooled to between about 0 and about −10° C. Phenylmagnesium bromide (3M, ether, 6 equiv) was added at a rate (e.g. over 20 minutes) to keep the temperature between 0 and −10° C. The reaction was then allowed to warm to room temperature and stirred overnight. The mixture was then quenched with 4M HCl and filtered. The crude solids were placed in an ultrasonic bath with acetone and re-filtered. The residue was then dissolved in dichloromethane with 5 percent ethanol and washed gently with 10 percent HCl, and rotovaped dry. The solids were reslurried in hot DCM/EtOH, filtered to remove some solids, and the product was precipitated with heptane to give 48% theoretical yield having more than 98 percent. (E.g., 98.15 percent, average HPLC peak area integration). Melting point of the final product was 327-350° C. (decomposition). $^1$H, $^{13}$C, $^{31}$P NMR agree with the proposed structure.

The shuttle formed from this Example 3 was (2,5-dimethoxy-1,4-phenylene)bis(diphenylphosphine oxide).

Example 4

A 500 mL 3 neck flask was charged with tetraethyl (2,5-dimethoxy-1,4-phenylene)bis(phosphonate). A thermocouple and reflux condenser were attached. The flask was purged with nitrogen and the outlet gasses send to a NaOH$_{(aq)}$ trap. The solids were dissolved in thionyl chloride and the solution was heated to 65° C. with stirring. N,N-Dimethylformamide (about 4 equiv) was added via syringe pump over about 2 hours. The solution was kept at temperature for about 14 hours. The mixture was then cooled to room temperature.

The solids that precipitated from the reaction mixture were filtered under nitrogen and washed with about equal amounts of toluene and MTBE and dried under a nitrogen stream for 1 hour to give an off-white powder.

The crude intermediate was slurried in 2-methyltetrahydrofuran. The mixture was cooled to between 0 and −10° C. Methylmagnesium bromide (3M, ether, 6 equiv) was added at a rate (e.g., over 75 minutes) to keep the temperature between −5° C. and about 5° C. The reaction was then allowed to warm to room temperature and stirred overnight. The mixture was then quenched with methanol and filtered. The crude solids were extracted into dichloromethane with 10 percent ethanol and filtered. The product was precipitated with heptane and filtered. The filtrate was dried and recombined with the solids. The combined material was dissolved in warm IPA and slurried with of Amberlyst resin. The amberlyst was filtered off and the filtrate treated with activated charcoal and filtered. The dried filtrate was slurried in acetone and filtered to give the purified solid (at about 45 percent yield) having a purity greater than 99 percent (e.g., 99.44 percent average HPLC peak area integration). GC/MS>99.9% peak area, m/z 290. Melting point 208-210° C. (decomposition). $^1$H, $^{13}$C, $^{31}$P NMR agree with the proposed structure.

The shuttle formed from this Example 4 was (2,5-dimethoxy-1,4-phenylene)bis(dimethylphosphine oxide).

Example 5

Crude ArP(O)Cl$_2$ intermediate was transferred to a clean 250 mL 3 neck flask and slurried in 2-methyltetrahydrofuran. The mixture was cooled to between about 0 and about −10° C. 4-Fluorophenylmagnesium bromide (2M, ether, 6 equiv) was added slowly over 75 minutes to keep the temperature between about −5° C. and 5° C. The reaction was then allowed to warm to room temperature and stirred overnight. The mixture was then quenched with methanol and rotovaped. The solids were partitioned between DCM and 10 percent HCl. The organic layers were dried and rotovaped. The crude solids were recrystallized from DCM/acetone, then DCM/hexane to give 22 percent yield having a purity better than 98 percent (e.g., purity 98.69% given an average HPLC peak area integration). Melting point was between about 278-281° C. $^1$H, $^{13}$C, $^{19}$F, $^{31}$P NMR agree with the proposed structure.

The shuttle formed from this Example 5 was (2,5-dimethoxy-1,4-phenylene)bis(bis(4-fluorophenyl)phosphine oxide).

With all compounds generated in Examples 2-5, kilogram amounts (more than 1 kg batches) of reasonably pure (greater than 97 percent) material were recovered from various processes.

Figure 7:
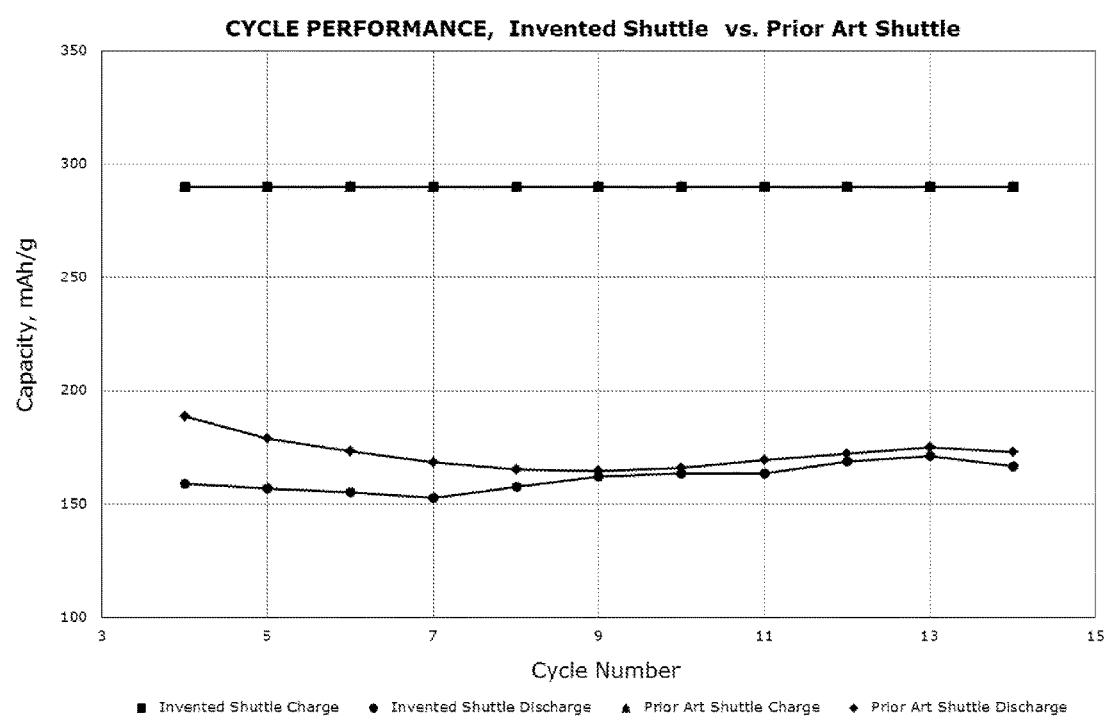
FIG. 7 is a graph depicting the electrochemical characteristics of a redox shuttle, in accordance with features of the present invention.

In operation, the method produced a shuttle which performs at the same level of efficiency as shuttles produced by more expensive protocols outlined supra. For example, FIG. 7 is a voltage graph which shows that voltage on each recharge cycle does not increase indefinitely when the invented shuttle is utilized. This means that the shuttle effect is intact.

FIG. 7 further shows repeated cycling before break down occurs at cycle 15. The similarity of the two curves shows that the invented material performs as well as materials developed by the inventors but using more expensive, less scalable protocols. For example, the "Invented Shuttle Charge" and the "Prior Art Shuttle Charge" curves overlay each other. Also, the discharge curves between the instant shuttle and the prior art are very similar.

In this particular cycling paradigm, meso-carbon micro beads comprise the anode, LiNi$_x$Co$_y$Mn$_z$O$_2$ (NCM, 0≤x,y,z<1) comprise the cathode material, and a LiPF$_6$-ethylene carbonate/elthymethyl carbonate (EC/EMC) mixture comprised the electrolyte. It was to this mixture that the invented shuttle was added in various solubility ranges.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A method for producing a molecule capable of undergoing reduction-oxidation when subjected to a voltage potential, the method comprising:
   a. phosphorylating hydroquinone to create a first intermediate compound;
   b. rearranging the first intermediate compound to an aryl-bis-(phosphonate) thereby creating a second intermediate compound comprising phosphorous alkoxy groups;
   c. alkylating the second intermediate compound;
   d. converting the alkoxy groups to halides; and
   e. substituting the halides to alkyl or aryl groups; wherein the entire method is performed at or above a lowest temperature wherein said lowest temperature is between approximately −10° C. and approximately −20° C.

2. The method as recited in claim 1 wherein at least four phosphorous alkoxy groups are converted to halides.

3. The method as recited in claim 1 further comprising a recrystallization step to produce the molecule having better than 99 percent purity.

4. The method as recited in claim 1 wherein step c is performed at or below a highest temperature, the highest temperature about 60° C.

5. The method as recited in claim 1 wherein the highest natural reaction temperature for the conversion step is between about 75 and about 80 C.

6. The method as recited in claim 1 wherein the alkoxy groups are phosphonate esters which are chlorinated to yield aryl bis(phosphonyl dichloride).

7. The method as recited in claim 1 wherein the halide is aryl bis(phosphonyl dichloride) and the dichloride does not need to be purified prior to the substitution step.

8. The method as recited in claim 1 wherein each of the alkyl groups bonded to phosphorous contain no more than 2 carbons.

9. The molecule as produced by the method of claim 1, whereby the molecule exhibits between about 10 and about 20 weight percent solubility in an electrolyte of a Lithium-ion battery.

10. The method of claim 1 wherein hydroquinone is 1-4 dihydroxy benzene.

11. The method of claim 1 wherein part c. is performed using solvents.

12. The method of claim 1 wherein the lowest temperature is about −15° C.

* * * * *